United States Patent
Rastogi et al.

(10) Patent No.: US 12,142,366 B2
(45) Date of Patent: Nov. 12, 2024

(54) DISTRIBUTED TRAINING OF SYSTEMS FOR MEDICAL IMAGE ANALYSIS

(71) Applicant: REMIDIO INNOVATIVE SOLUTIONS PVT. LTD., Bengaluru (IN)

(72) Inventors: Krishna Rastogi, Bengaluru (IN); Anand Sivaraman, Jalhalli Bangalore (IN)

(73) Assignee: Remidio Innovative Solutions Pvt. Ltd., Bengaluru (IN)

(*) Notice: Subject to any disclaimer, the term of this patent is extended or adjusted under 35 U.S.C. 154(b) by 723 days.

(21) Appl. No.: 17/275,584

(22) PCT Filed: Sep. 11, 2019

(86) PCT No.: PCT/IN2019/050659
§ 371 (c)(1),
(2) Date: Mar. 11, 2021

(87) PCT Pub. No.: WO2020/053887
PCT Pub. Date: Mar. 19, 2020

(65) Prior Publication Data
US 2021/0365734 A1  Nov. 25, 2021

(30) Foreign Application Priority Data
Sep. 11, 2018 (IN) .............................. 201841034268

(51) Int. Cl.
*G16H 30/40* (2018.01)
*A61B 3/00* (2006.01)
(Continued)

(52) U.S. Cl.
CPC .......... *G16H 30/40* (2018.01); *A61B 3/0025* (2013.01); *A61B 3/12* (2013.01); *G06F 18/2148* (2023.01);
(Continued)

(58) Field of Classification Search
CPC ...... G16H 30/40; G16H 50/20; A61B 3/0025; A61B 3/12; G06F 18/2148; G06N 20/00;
(Continued)

(56) References Cited

U.S. PATENT DOCUMENTS 8,296,247 B2 * 10/2012 Zhang .................... G06N 20/00
706/924
8,543,519 B2   9/2013 Guyon et al.
(Continued)

FOREIGN PATENT DOCUMENTS

WO   WO 2018015414 A1   1/2018
WO   WO 2018093865 A1   5/2018

OTHER PUBLICATIONS

International Search Report and Written Opinion for Application No. PCT/IN2019/050659, mailed Dec. 17, 2019, 9 pages.
(Continued)

*Primary Examiner* — Casey L Kretzer
(74) *Attorney, Agent, or Firm* — Seed Intellectual Property Law Group LLP

(57) ABSTRACT

The present subject matter provides systems and methods for distributed training of artificial intelligence (AI) systems for medical image analysis. The systems allow for offline prediction of abnormalities of medical images on a local AI system associated with an imaging device (102). In one example, the local AI system (100) extracts image parameters from the analyzed medical images and sends it to a global AI system (120) for training a global AI model. In another example, the local AI system (100) retrains a previously trained local AI model based on the image parameters to obtain a local AI model. Model parameters are extracted from the local AI model and are sent to the global
(Continued)

AI system to retrain a global AI model. The retrained global AI model is deployed back to the local AI system (100) for updating the local AI model.

12 Claims, 6 Drawing Sheets

(51) Int. Cl.
    *A61B 3/12*     (2006.01)
    *G06F 18/214*     (2023.01)
    *G06N 20/00*     (2019.01)
    *G06T 7/00*     (2017.01)
    *G16H 50/20*     (2018.01)

(52) U.S. Cl.
    CPC .......... *G06N 20/00* (2019.01); *G06T 7/0012* (2013.01); *G16H 50/20* (2018.01); *G06T 2207/20081* (2013.01); *G06T 2207/30041* (2013.01); *G06V 2201/03* (2022.01)

(58) Field of Classification Search
    CPC ......... G06T 7/0012; G06T 2207/20081; G06T 2207/3004; G06V 2201/03
    See application file for complete search history.

(56) References Cited

U.S. PATENT DOCUMENTS

2015/0242760 A1\*   8/2015   Miao ..................... G06N 20/00
    706/12
2018/0018590 A1   1/2018   Szeto et al.
2020/0302576 A1\*   9/2020   Xu ......................... G06N 3/084

OTHER PUBLICATIONS

Office Action, dated Jun. 12, 2021, for Indian Patent Application No. 201841034268. (5 pages) (with English Translation).

\* cited by examiner

DISTRIBUTED TRAINING OF SYSTEMS FOR MEDICAL IMAGE ANALYSIS

TECHNICAL FIELD

The present subject matter relates, in general, to training of systems for medical image analysis and, in particular, to distributed training of artificial intelligence systems for detection of abnormalities based on medical image analysis.

BACKGROUND

Generally, artificial intelligence (AI) systems are used to learn from a large dataset of medical images and update a model to predict/detect outcomes, such as abnormalities in the medical images. An AI system is typically deployed in the cloud and is connected to multiple medical imaging devices over a network. The AI system receives an image to be analyzed from a medical imaging device, analyzes the image based on the model to detect abnormalities, and provides the diagnosis back to the medical imaging device. In this process, the AI system can also further learn and update the model to increase its accuracy over time. However, it is also important to maintain privacy of a patient in this process. Further, the AI system needs to analyze a large number and wide variety of images to develop high sensitivity and specificity over time.

Moreover, to use the analytical capabilities of the AI system, the medical imaging device has to be connected to the AI system over a network, such as an Internet or mobile network. Further, as medical images are typically of high resolution and large size, the network connectivity has to be good enough for the medical imaging device to be able to transmit the medical image to the AI system. However, often, medical imaging devices, such as mobile healthcare devices, deployed in remote locations do not have any Internet or Mobile connectivity to use the AI system deployed on a cloud. Such medical imaging devices may collect the images over a period and transmit the images to the AI system when the network connectivity becomes available. This leads to a significant time lag in the diagnosis becoming available to the healthcare provider and the patient. This is inconvenient to both the healthcare provider and the patient and not desirable particularly in emergency situations or in situations where the healthcare provider is available on a temporary basis.

BRIEF DESCRIPTION OF FIGURES

The detailed description is provided with reference to the accompanying figures. In the figures, the left-most digit(s) of a reference number identifies the figure in which the reference number first appears. The same numbers are used throughout the figures to reference like features and components.

DETAILED DESCRIPTION

Figure 1A:
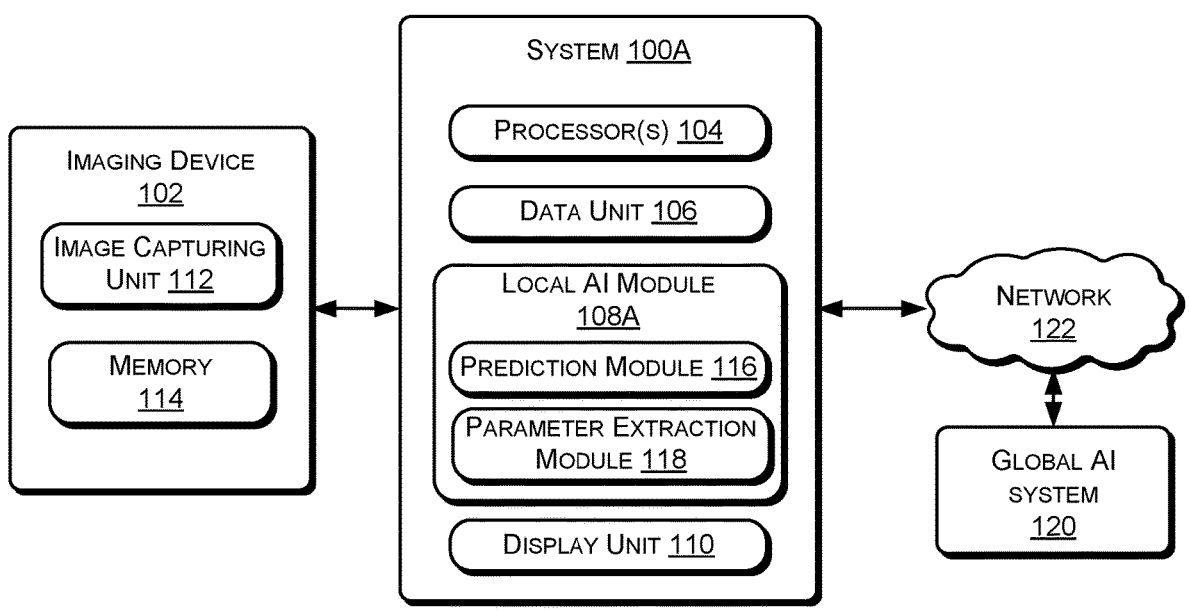
FIG. 1A illustrates an example system for medical image analysis, in accordance with an example of the present subject matter.

Aspects of distributed training of systems for medical image analysis are described herein. The network environment, systems, and methods of the present disclosure allow for offline prediction of abnormalities/analysis of the medical images on a local AI system associated with a medical imaging device.

In one example, the local AI system can extract image parameters out of the medical images being analyzed and can send the parameters to a global AI system on a cloud network for training and updating a global AI model. Thus, instead of actual patient data, image parameters are transferred to the cloud to maintain data privacy. The global AI model, which is updated based on image parameters received from multiple local AI systems, may be then used to update a local AI model in the local AI system. Image parameters as used herein refer to features of the image that are represented as data points and hence can be easily transferred over a network rather than transferring the whole image.

In another example, the local AI model used by the local AI system can be locally trained and updated. In this case, the local AI system learns from every captured image and updates local AI model parameters. When the change in local AI model parameters increases beyond a threshold, the local AI model parameters are sent to the global AI system on a cloud network. Thus, in this case, instead of actual patient data, model parameters are transferred to the cloud to maintain data privacy. A feedback loop is also provided between the local AI system and the global AI system to update a global AI model based on the local AI model parameters received from multiple local AI systems. Model parameters as used herein refer to weights of the image parameters and thus the model parameters define the AI model to which they relate.

The global AI model can be used to update the local AI models periodically or when network connectivity is available. Hence, the present subject matter provides for distributed training, maintaining data privacy, ensuring fast analysis of medical images remotely, and updating local AI models using learning gathered by the global AI system from multiple local AI models or image parameters received from multiple local AI systems.

Aspects of the present subject matter are further described in conjunction with FIGS. 1A-5. It should be noted that the description and figures merely illustrate the principles of the present subject matter. It will thus be appreciated that various arrangements that embody the principles of the present subject matter, although not explicitly described or shown herein, can be devised from the description and are included within its scope. Moreover, all statements herein reciting principles, aspects, and implementations of the present subject matter, as well as specific examples thereof, are intended to encompass equivalents thereof. Further, for the sake of simplicity, and without limitation, the same numbers are used throughout the drawings to reference like features and components.

FIG. 1A illustrates an example system 100A for medical image analysis. The system 100A may be referred to as a local AI system and may be associated with a medical imaging device 102, also referred to as an imaging device 102. The system 100A can be a desktop computer, a server, a laptop computer, a mobile device, or the like. The medical imaging device may be an ophthalmic imaging device, a radiology imaging device, a mobile device with a camera and an application for capturing medical images, or the like. In one example, the system 100A may be connected to the imaging device 102 directly or through a network. The network, though not shown, may be a private network, a home network, an office network, a local area network (LAN), a Wi-Fi network, a short range wireless network like Bluetooth, or the like. There may also be more than one imaging device 102 associated with the system 100A. In one implementation, the system 100A and imaging device 102 may be integrated into a single device, such as a mobile device.

Among other components, the system 100A includes a processor 104, a data unit 106, a local AI module 108A, and a display unit 110. Further, the imaging device 102 may include an image capturing unit 112 and a memory 114. The image capturing unit may be a camera or a scanner or the like. Each of the system 100A and imaging device 102 may include other hardware, such as other processing units, interfaces, modules, data, etc., which are not shown for the sake of brevity. Further, some or all of the components may be shared between the system 100A and the imaging device 102 depending on the implementation.

The imaging device 102 may obtain medical images, such as ophthalmic images or radiology images using the image capturing unit 112 and may store the medical image in the memory 114. The imaging device 102 may then provide the medical image to the system 100A for analysis and diagnosis based on the prediction of abnormalities. The system 100A may store the received image in the data unit 106. The local AI module 108A can receive the image and use it for offline prediction using a local AI model stored in the data unit 106. For example, a prediction module 116 may perform the prediction of abnormalities from the medical image by using the image as an input to the local AI model and may provide the results to the display unit 110 for displaying to a user, such as a healthcare provider.

In one example, the local AI module 108A may include parameter extraction module 118 that may extract image parameters or features relevant for prediction from the medical image. For example, parameter extraction techniques include Histogram of oriented gradients (HOG), Speeded-up robust features (SURF), Local binary patterns (LBP), Haar wavelets, Color histograms, and the like may be used to obtain image parameters. In one example, in case of HOG for retinal images, the pathologies with blood and vessels may be extracted to create a feature set for every image. The features set, also referred to as image parameters, generated by the parameter extraction module 118 can be used by the prediction module 116 for offline prediction using the local AI model.

Further, the image parameters may be sent to global AI system 120, for example, over a network 122, for training and updating a global AI model. In one example, the system 100A may upload the image parameters to a global AI system 120 when the system 100A is connected to the global AI system 120, for example over network 122, to retrain the global AI model. In another example, the local AI system 100A may send the image parameters periodically or when it is polled by the global AI system 120. As will be understood, the image parameters shared by the system 100A are representative of anonymized patient data and thus help in maintaining data privacy while at the same time ensuring that patient data is available for training the global AI model. Further, as the amount of data to be transmitted for sending image parameters is much less than that for sending the image itself, the local AI system 100A uses less network resources and can complete the transmission quickly. The retrained global AI model may then be deployed back in the system 100A to update the local AI model.

Since the global AI model gets retrained based on image parameters received from multiple local AI systems like the system 100, the retrained global AI model that is deployed back into the system 100A is able to handle a wider range of predictions. Further, as the system 100A only performs extraction of image parameters and prediction of abnormalities using the local AI model based on the image parameters, it may not need a large amount of processing power or speed. Hence, the overall cost of the system 100A deployed at remote locations may also be reduced.

While a single system 100A is shown in FIG. 1A, it will be understood that multiple systems 100A may be communicatively coupled to the global AI system 120 and will each include their respective local AI module 108A with a local AI model. The training of the global AI model using image parameters received from different local AI systems is described below with reference to FIG. 2.

Figure 1B:
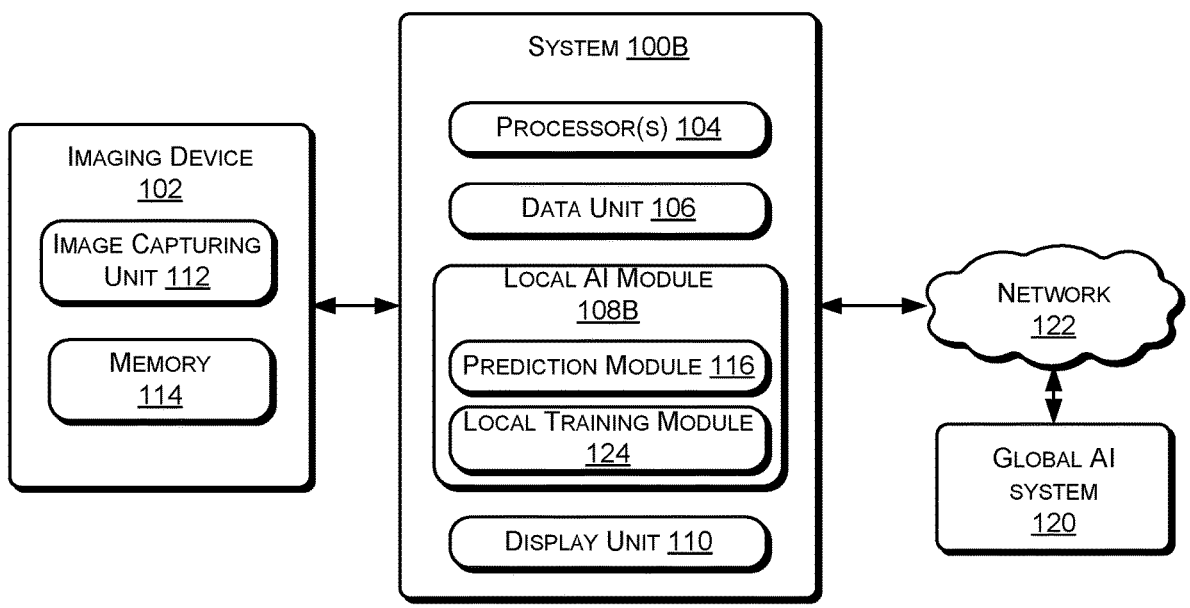
FIG. 1B illustrates an example system for medical image analysis, in accordance with an example of the present subject matter.

FIG. 1B illustrates an example system 100B for medical image analysis. Like the system 100A, the system 100B may be referred to as a local AI system and may be associated with a medical imaging device 102, also referred to as an imaging device 102. The system 100B can be a desktop computer, a server, a laptop computer, a mobile device, or the like. The medical imaging device may be an ophthalmic imaging device, a radiology imaging device, a mobile device with a camera and an application for capturing medical images, or the like. In one example, the system 100B may be connected to the imaging device 102 directly or through a network. The network, though not shown, may be a private network, a home network, an office network, a local area network (LAN), a Wi-Fi network, a short range wireless network like Bluetooth, or the like. There may also be more than one imaging device 102 associated with the system 100B. In one example, the system 100B and imaging device 102 may be integrated into a single device, such as a mobile device.

Among other components, the system 100B includes a processor 104, a data unit 106, a local AI module 108B, and a display unit 110. Further, the imaging device 102 may include an image capturing unit 112 and a memory 114. The image capturing unit may be a camera or a scanner or the like. Each of the system 100B and imaging device 102 may include other hardware, such as other processing units, interfaces, modules, data, etc., which are not shown for the sake of brevity. Further, some or all of the components may be shared between the system 100B and the imaging device 102 depending on the implementation.

The imaging device 102 may obtain medical images, such as ophthalmic images or radiology images using the image capturing unit 112 and may store the medical image in the memory 114. The imaging device 102 may then provide the medical image to the system 100B for analysis and diagnosis based on the prediction of abnormalities. The system 100B may store the received image in the data unit 106. The local AI module 108B can receive the image and use it for offline prediction using a local AI model stored in the data unit 106 as discussed above. For example, a prediction module 116 may perform the prediction and may provide the results to the display unit 110 for displaying to a user, such as a healthcare provider. In this example, the prediction module 116 or a separate module (similar to the parameter extraction module 118) may extract image parameters as discussed with reference to FIG. 1A to be fed to the local AI model for prediction of the abnormalities.

Further, the local AI module 108B may include a local training module 124 that may use one or more medical images from the data unit 106 to re-train a previously trained local AI model using the extracted image parameters of the one or more medical images to obtain a local AI model. In one example, the system 100B may obtain model parameters that are updated upon re-training the local AI model. In an example, the model parameters may be obtained using the hyperparameter settings such as horizontal and vertical shift, horizontal and vertical flip, random rotation, random brightness, random zoom and the like. In an example, an AI model may be represented as a mathematical function of variables with weights attached to each variable for predicting an outcome. In the present subject matter, the variables may be the image parameters, the weights may be the model parameters, and the outcome may be the presence or absence of an abnormality in the medical image. Thus, when trained using image parameters for multiple patients, the model parameters may be representative of anonymized patient data.

The model parameters may be then sent to the global AI system 120 for re-training of the global AI model. In one example, when the change in the model parameters increases beyond a threshold, the model parameters are sent to a global AI system 120. In another example, the model parameters may be sent periodically or when the local AI system is polled by the global AI system. At the global AI module, the received model parameters may be assessed against a ground truth of a test data sets prior to re-training of the global AI model.

The model parameters may be uploaded, for example, when the system 100B is connected to the global AI system 120 over network 122, to retrain the global AI model. Since the system 100B shares model parameters and not the images themselves, it helps in maintaining data privacy while at the same time ensuring that patient data is available for training the global AI model. Further, transmission of the model parameters consumes much less resources than the transmission of the images itself. In one example, the system 100B may have a higher processing power than the system 100A to enable it to re-train the local AI model.

While a single system 100B is shown in FIG. 1B, it will be understood that multiple systems 100B may be communicatively coupled to the global AI system 120 and will each include their respective local AI module 108B with a local AI model. The training of the global AI model using image or model parameters received from different local AI systems is described below with reference to FIG. 2.

Figure 2:
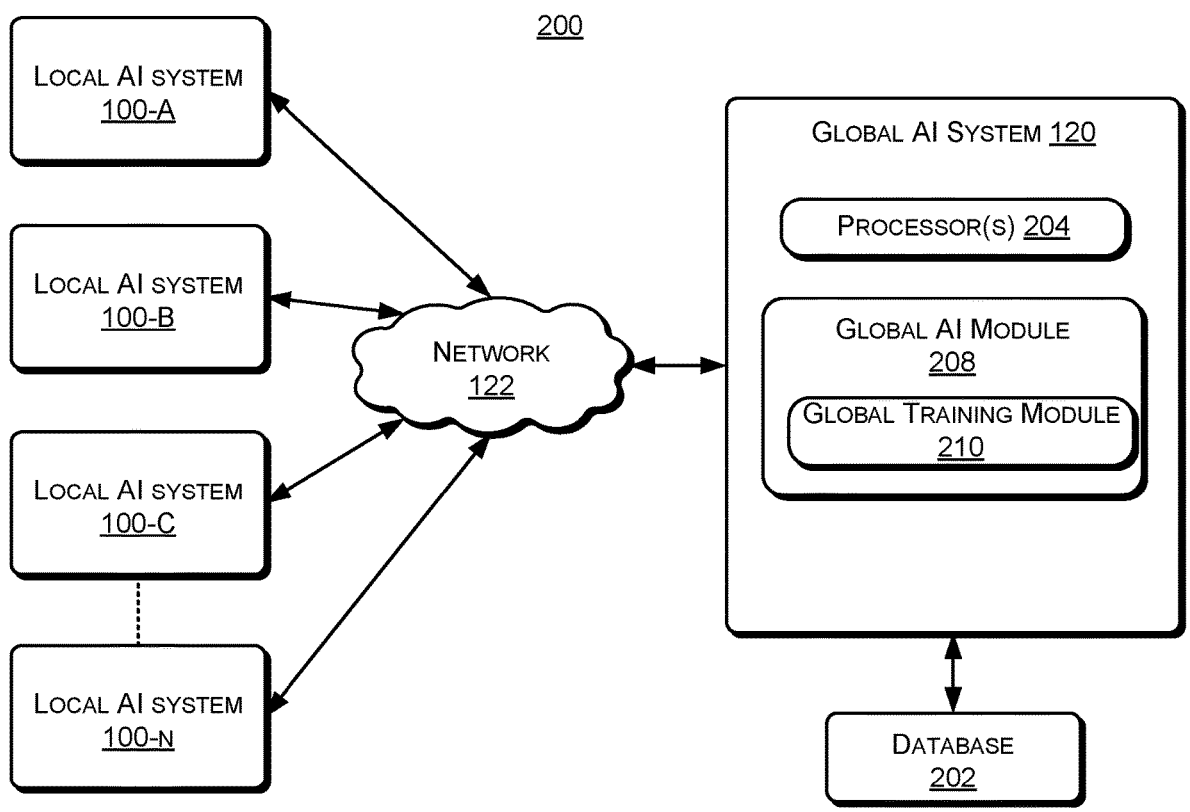
FIG. 2. illustrates an example network environment for distributed training of systems for medical image analysis, in accordance with an example of the present subject matter.

FIG. 2. illustrates an example network environment 200 for distributed training of systems for medical image analysis, in accordance with an example of the present subject matter. As shown in FIG. 2, a plurality of local AI systems 100-a, 100-b . . . 100-n, collectively referred to as local AI systems 100 or individually as a local AI system 100, may be communicatively coupled to the global AI system 120 over the network 122. A local AI system 100 may be similar to the system 100A or the system 100B. i.e., the local AI system 100 may provide image parameters or model parameters to the global AI system 120 for training of the global AI model.

In one example, network 122 may be a cloud network and may include various computing devices, storage devices, and networking devices, which will be understood but are not shown for simplicity. The global AI system 120 may be a part of the network 122 or may be coupled to it. Further, the global AI system 120 may be coupled to a database 202. The global AI system 120 itself may be a distributed system. Similarly, the database 202 may be a distributed storage system.

In one example, the global AI system 120 may include a processor 204 and a global AI module 208. Further, the global AI module may include a global training module 210. Initially, the global AI system 120 may be trained based on reference images and an initial global AI model may be generated and deployed in the local AI systems 100 as the local AI model for prediction of abnormalities locally based on image analysis as discussed above.

As discussed earlier, each local AI system 100 will include its respective local AI module 108A or 108B, also referred to as local AI module 108, that analyzes images received from the respective imaging device to predict abnormalities based on the local AI model stored in respective data unit. Further, based on the image analyses, the local AI module 108 may either send features (i.e., image parameters) to the global AI system 120 or may locally re-train the previously trained local AI model to obtain local AI model and send model parameters to the global AI system 120. Thus, the parameters shared by each local AI system 100 with the global AI system 120 may be either image parameters or model parameters. In an example, the image parameters are sent to the global AI system, when the local AI system does not have the power to retrain the previously training local AI model and therefore cannot obtain the model parameters.

In one example, the parameters may be sent from the local AI systems 100 to the global AI system 120 each time a local AI system 100 is connected to the network 122. In another example, the parameters may be sent periodically upon availability of the connection to the network 122. In yet another example, the parameters may be sent after a certain number of images have been captured and analyzed locally.

In one example, the global AI system 120 may receive the parameters from the different local AI systems 100 and the global training module 210 may retrain a global AI model based on the different parameters. In an example, the retrained global AI model may be represented as a mathematical function of variables with weights attached to each variable for predicting an outcome. In the present subject matter, the variables may be the image parameters, the weights may be the model parameters, and the outcome may be the presence or absence of an abnormality in the medical image. Thus, the image parameters and the model parameters obtained from the different local AI systems 100 may be used to retrain the global AI model and obtain updated weights and variables.

For example, when the model parameters for local model $M^k$ are received from K number of local AI systems 100A-N, the global model $M^G$ may be updated as $$M^G \leftarrow \sum_{k=1}^{K} \frac{n_k}{n} M^k$$

Where, k=a local AI system,
$n_k$=number of data points received from local system k and n=total number of data points received from all the K local systems Accordingly, the global AI model gets retrained based on the wide variety of images represented by the parameters. Each time the global AI model is updated and re-shared with the local AI system, it may be referred to as a round. It will be understood that multiple rounds of updates may happen and so over a period of time the global AI model and each of the local AI models become increasingly capable of detecting different kinds of abnormalities. The received parameters and the retrained global AI model may be stored in the database 202 for future reference.

The database 202 may also include reference images and other data as may be required for the initial training of the global AI system 120. The database 202 may serve as a repository for storing data that may be fetched, processed, received, or created by global AI system 120 or received from the global AI system 120 or any connected devices. While the database 202 is shown as external to the global AI system 120, it will be understood that the database 202 may be a part of the global AI system 120 and can be accessed by the global AI system 120 using various communication means. Additionally, the global AI system 120 may include various interfaces, memories, other data, and the like, which are not shown for brevity.

The interfaces may include a variety of computer-readable instructions-based interfaces and hardware interfaces that allow interaction with other communication, storage, and computing devices, such as network entities, web servers, databases, and external repositories, and peripheral devices. The memories may include any non-transitory computer-readable medium including, for example, volatile memory (e.g., RAM), and/or non-volatile memory (e.g., EPROM, flash memory, etc.). The memories may include an external memory unit, such as a flash drive, a compact disk drive, an external hard disk drive, or the like. The other modules may include modules for operation of the global AI system 120, such as operating system, and other applications that may be executed on the global AI system 120. Other data may include data used, retrieved, stored, or in any way manipulated by the global AI system 120.

Once the global AI model is retrained, the global AI system 120 can send the retrained global AI model to the local AI systems 100 for updating the local AI model. Thus, all the local AI models also get updated.

Sharing of the parameters from the local AI systems 100 to the global AI system 120 for retraining the global AI model helps in distributed training of the global AI model. It also ensures cross-training and better specificity and sensitivity as a wide set of underlying images are used in the retraining. For example, the different local AI systems 100 may be used in different remote locations, where different types of abnormalities or medical conditions may be encountered. By retraining the global AI model based on the parameters representative of the different abnormalities encountered in the different remote locations and updating the local models based on the retrained global AI model, each local AI model can also predict abnormalities that may not be commonly encountered in the remote location where it is deployed.

In the above process, since only the parameters are exchanged between the different systems instead of images, the anonymity of patient data is maintained. Further, the network bandwidth requirement is also considerably reduced. Also, processing and storage requirements in the cloud are reduced, thereby making it more efficient.

Figure 3:
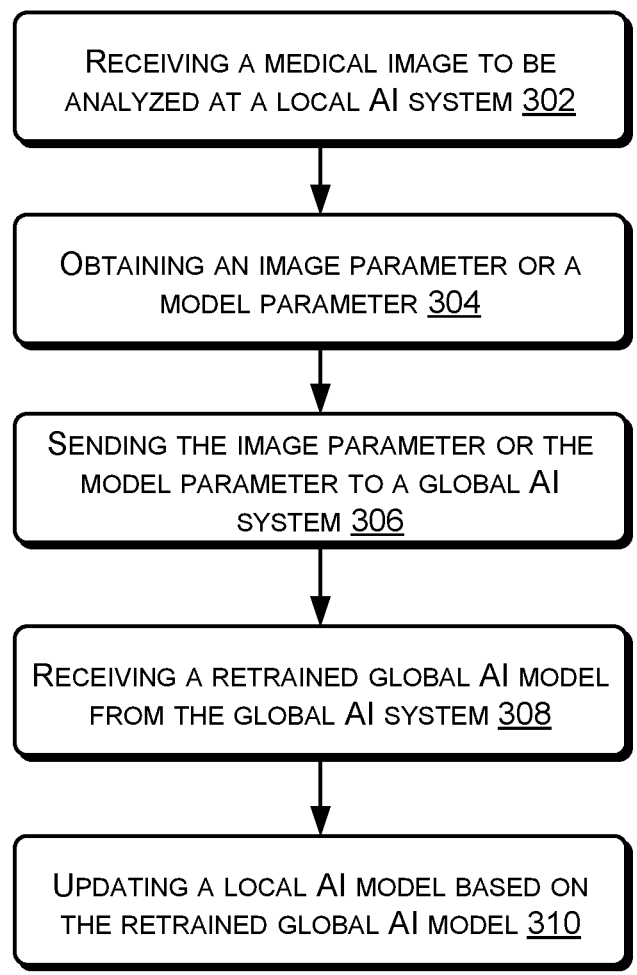
FIG. 3. illustrates a method of distributed training of systems for medical image analysis, in accordance with an example of the present subject matter.
Figure 4A:
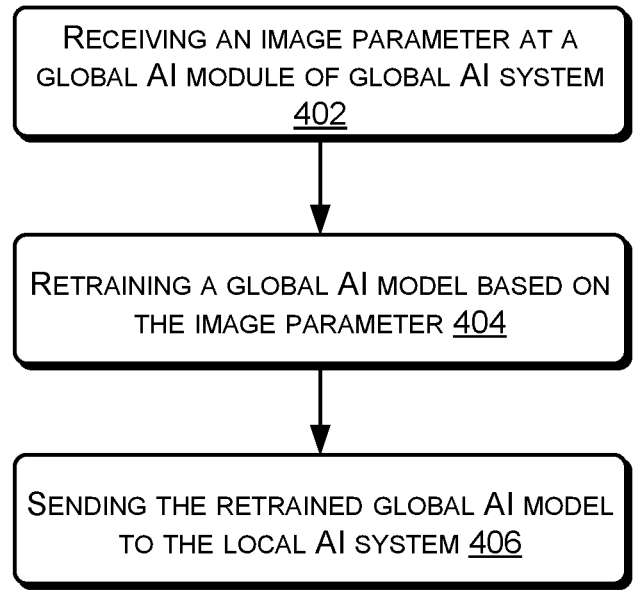
FIGS. 4a and 4b illustrates methods for distributed training of artificial intelligence (AI) system at a global AI system for medical image analysis, in accordance with an example of the present subject matter.
Figure 4B:
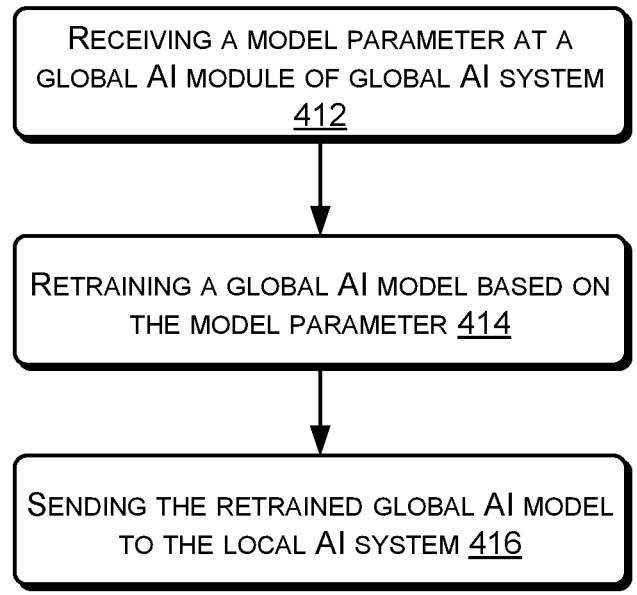

FIGS. 3, 4A, and 4b illustrate example methods 300, 400, and 410 for distributed training of artificial intelligence (AI) system for medical image analysis, according to example implementations of the present subject matter. The order in which the methods 300, 400, and 410 are described is not intended to be construed as a limitation, and some of the described method steps can be combined in a different order to implement the methods or alternative methods. Furthermore, the methods 300, 400 and 410 may be implemented in any suitable hardware, computer readable instructions, or combination thereof. The steps of methods 300, 400, and 410 may be performed by either a system under the instruction of machine-executable instructions stored on a non-transitory computer readable medium or by dedicated hardware circuits, microcontrollers, or logic circuits. Herein, some examples are also intended to cover non-transitory computer readable medium, for example, digital data storage media, which are computer readable and encode computer-executable instructions, where said instructions perform some or all of the steps of the methods 300, 400, and 410. While the methods 300, 400, and 410 may be implemented in any device, the following description is provided in the context of local AI system 100 and global AI system 120 as described earlier with reference to FIGS. 1A, 1B, and 2 for case of discussion.

FIG. 3 illustrates a method 300 for distributed training of artificial intelligence (AI) system at a local AI system for medical image analysis, in accordance with an example implementation of the present subject matter. At step 302, a medical image to be analyzed for abnormalities is received. In an example, the medical image such as ophthalmic image or radiology image are received from an imaging device at the local AI system. In an example, the imaging device may be an ophthalmic imaging device, a radiology imaging device, a mobile device with a camera and an application for capturing medical images, or the like. At step 304, an image parameter or a model parameter is obtained. In an example, the image parameter is extracted from the medical image for example, using common parameter extraction techniques such as Histogram of oriented gradients (HOG), Speeded-up robust features (SURF), Local binary patterns (LBP), Haar wavelets, Color histograms, and the like. In another example, the model parameter is extracted from a local AI model. For example, a previously trained local AI model may be retrained based on the image parameters to obtain the local AI model and the model parameters are then extracted from the local AI model. In an example, the model parameters may be obtained using the hyperparameter settings such as horizontal and vertical shift, horizontal and vertical flip, random rotation, random brightness, random zoom and the like Further, at step 306, the image parameter or the model parameter is shared to a global AI system. In an example, the image parameter or the model parameter is shared by a local AI module of the local AI system. At step 308, a retrained global AI model is received from the global AI system 120. In an example, the retrained global AI model is retrained based on the image parameter or the model parameter. In another example, the retrained global AI model is retrained in a global AI module of the global AI system. The global AI system may be deployed on a cloud or a server and is accessible by the local AI system via network. Next, at step 310, a local AI model may be updated based on the retrained global AI model. Since the global AI model gets trained based on the image parameter or the model parameter from multiple local AI systems, the retrained global AI model that is deployed back into the local AI system can handle a wider range of predictions of abnormalities of the medical image.

FIGS. 4a and 4b illustrates methods (400, 410) for distributed training of artificial intelligence (AI) system at a global AI system 120 for medical image analysis. FIG. 4*a* illustrates the method 400 of distributed training of AI system when an image parameter is used for retraining at the global AI system. At step 402, an image parameter is received at a global AI module of the global AI system. In an example the image parameter is extracted from a medial image using common parameter extraction techniques such as Histogram of oriented gradients (HOG), Speeded-up robust features (SURF), Local binary patterns (LBP), Haar wavelets, Color histograms, and the like. At step 404, a global AI model is retrained based on the image parameter to obtain a retrained global AI model. Further, at step 406, the retrained global AI model is sent to a local AI system. In an example, after sending the retrained global AI model, a local AI model may be updated based on the retrained global AI model.

FIG. 4*b* illustrates the method 410 of distributed training of AI system when a model parameter is used for retraining at the global AI system. At step 412, a model parameter is received at the global AI system. In an example, the model parameter is extracted from a local AI model and the local AI module is obtained by retraining a previously trained local AI model based on the extracted image parameter. In another example, the model parameters may be obtained using the hyperparameter settings such as horizontal and vertical shift, horizontal and vertical flip, random rotation, random brightness, random zoom and the like. At step 414, a global AI model is retrained based on the model parameter to obtain a retrained global AI model. Further, at step 416, the retrained global AI model is sent to a local AI system. In an example, after sending the retrained global AI model, a local AI model may be updated based on the retrained global AI model.

Figure 5:
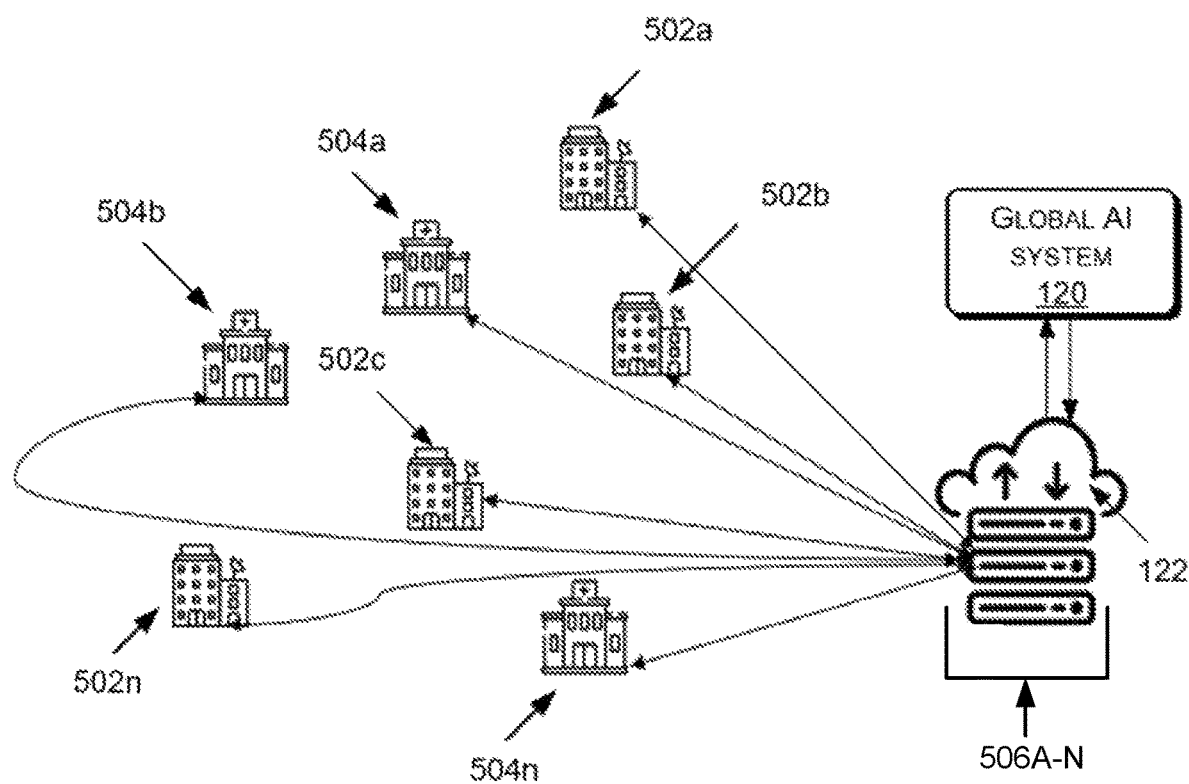
FIG. 5 depicts an example implementation of distributed training of artificial intelligence (AI) system at a global AI system, in accordance with an example of the present subject matter.

FIG. 5 depicts an example implementation of distributed training of artificial intelligence (AI) system at a global AI system. According to FIG. 5, detection of abnormalities from fundus images of diabetic retinopathy patients are explained using the distributed training of AI system. In an example, vision centers and hospitals such as diabetic retinopathy screening vision centers (502*a-n*), eye hospitals (504*a-n*) are used for explaining the example implementation. The vision centers (502*a-n*) and hospitals (504*a-n*) comprise one or more imaging device for capturing the fundus images of the eye. Further, the vision centers (502*a-n*) and hospitals (506*a-n*) comprises plurality of local systems that are adapted to extract image parameters from the captured fundus images. In an example, the image parameters are extracted from the fundus images for example, using common parameter extraction techniques such as Histogram of oriented gradients (HOG), Speeded-up robust features (SURF), Local binary patterns (LBP), Haar wavelets, Color histograms, and the like. The image parameters are then directly sent to the global AI system for retraining a global AI model.

In one example, the plurality of local systems retrains a previously trained local AI models based on the extracted image parameters to obtain a plurality of local AI models. Further, model parameters are extracted from the plurality of local AI models. For example, the model parameters may be obtained using the hyperparameter settings such as horizontal and vertical shift, horizontal and vertical flip, random rotation, random brightness, random zoom and the like. In another example, the fundus images may be labeled from various doctors of vision centers and hospitals. The labelling may be done as intermediate to expert level in diagnosing abnormalities in different stages of diabetic retinopathy. The labelled data may be then used to update the model parameters.

Further, the image parameters or the model parameters of the plurality of local AI models 506A-N are sent to the global AI system 120 for retraining a global AI model and the retrained global AI model is shared back to the plurality of local AI systems for updating the local AI models. In an example, when the change in local AI model parameters increases beyond a threshold, the model parameters are sent to the global AI system. In an example, the global AI model is then updated by calculating best performing model parameters among the local models from different hospitals, vision centers etc. In an example, the global AI system 120 is deployed on a cloud or a server and is accessible by the plurality of local AI systems via network 112.

Thus, using the methods and systems of the present subject matter, distributed training of systems can be provided for more efficient training of AI models even in case of remote deployment of local AI systems. Since the local AI system shares image parameters or model parameters and, not the images themselves, it helps in maintaining data privacy while at the same time ensuring that patient data is available for training the global AI model.

Although implementations for distributed training of systems for medical image analysis have been described in language specific to structural features and/or methods, it is to be understood that the invention is not necessarily limited to the specific features or methods described. Rather, the specific features and methods are disclosed and explained in the context of a few example implementations.

The invention claimed is:

1. A method for distributed training of artificial intelligence (AI) system at a local AI system for medical image analysis, the method comprising:
    receiving, by a local AI system, a medical image to be analyzed;
    obtaining, by the local AI system, a model parameter, wherein the model parameter is weight attached to an image parameter, wherein the image parameter corresponds to a plurality of features associated with the medical image and are represented as a set of data points determined by the local AI system;
    in response to detecting, by the local AI system, a change in a value of the model parameter corresponding to the local AI system being above a threshold value, the method further comprises:
    sending, by the local AI system, the model parameter to a global AI system without the medical image itself;
    receiving, by the local AI system, a retrained global AI model from the global AI system; and
    updating, by the local AI system, a local AI model based on the retrained global AI model.

2. The method as claimed in claim 1, wherein the medical image is one of ophthalmic images and radiology images that are received from an imaging device.

3. The method as claimed in claim 1, wherein obtaining the model parameter comprises:
    extracting, by the local AI system, the image parameter from the medical image to be analyzed;
    retraining, by the local AI system, a previously trained local AI model based on the image parameter to obtain the local AI model; and
    extracting, by the local AI system, the model parameter from the local AI model.

4. The method as claimed in claim 3, wherein the image parameter is extracted using at least one of Histogram of oriented gradients, Speeded-up robust features, local binary patterns, Haar wavelets, or Colour histograms.

5. The method as claimed in claim 3, wherein the model parameter is extracted using hyperparameter settings comprising one or more of horizontal and vertical shift, horizontal and vertical flip, random rotation, random brightness, or random zoom.

6. A method for distributed training of an artificial intelligence (AI) system at a global AI system for medical image analysis, the method comprising:
  receiving, by a global AI system, model parameters from a plurality of local AI systems in response to detecting a change in a value of a model parameter corresponding to a local AI system being above a threshold value, wherein the model parameters are weights attached to image parameters, wherein the image parameters correspond to a plurality of features associated with medical images and are represented as a set of data points determined by the plurality of local AI systems;
  retraining, by the global AI system, a global AI model based on the model parameters; and
  sending, by the global AI system, the retrained global AI model to the plurality of local AI systems.

7. The method as claimed in claim 6, further comprising in response to the sending, updating local AI models of the plurality of local AI systems based on the retrained global AI model.

8. A local artificial intelligence (AI) system for distributed training for medical image analysis, the local AI system comprising:
  a local AI module, configured to receive a medical image to be analyzed from an imaging device;
  a parameter extraction module, configured to extract an image parameter from the analyzed medical image, wherein the image parameter corresponds to a plurality of features associated with the medical image and are represented as a set of data points determined by the local AI system;
  a prediction module, configured to offline predict abnormalities in the analyzed medical image;
  a local training module, configured to retrain a previously trained local AI model based on the image parameter for obtaining a local AI model and to extract a model parameter from the local AI model, wherein the model parameter is weight attached to the image parameter; and the local training module to:
  detect a change in a value of the model parameter corresponding to the local AI system being above a threshold value; and
  in response to the detection, share the model parameter to a global AI system, wherein the local training module is adapted to receive a retrained global AI model from the global AI system for updating the local AI model.

9. The local AI system as claimed in claim 8, further comprising a display unit to display the prediction of abnormalities in the analyzed medical image.

10. The local AI system as claimed in claim 8, further comprising a data unit to store the medical image and the local AI model.

11. A global artificial intelligence (AI) system for distributed training for medical image analysis, the global AI system comprising,
  a global AI module, to receive model parameters from a plurality of local AI systems in response to detecting a change in a value of a model parameter corresponding to a local AI system being above a threshold value, wherein the model parameters are weights attached to image parameters, wherein the image parameters correspond to a plurality of features associated with medical images and are represented as a set of data points determined by the plurality of local AI systems; and
  a global training module, to retrain a global AI model based on the model parameters, wherein the global training module is adapted to share the retrained global AI model to the plurality of local AI systems for updating local AI models.

12. The global AI system as claimed in claim 11, wherein the global AI system is deployed on a cloud or a server and is accessible by the plurality of local AI systems via network.

* * * * *